United States Patent [19]

Fabinski et al.

[11] Patent Number: 5,077,469
[45] Date of Patent: Dec. 31, 1991

[54] CALIBRATING A NONDISPERSIVE INFRARED GAS ANALYZER

[75] Inventors: Walter Fabinski, Kriftel; Guenter Bernhardt, Frankfurth, all of Fed. Rep. of Germany

[73] Assignee: Hartmann & Braun AG, Frankfurt am Main, Fed. Rep. of Germany

[21] Appl. No.: 591,295

[22] Filed: Oct. 1, 1990

[30] Foreign Application Priority Data

Sep. 30, 1989 [DE] Fed. Rep. of Germany ....... 3932838

[51] Int. Cl.$^5$ ............................................. G01N 21/61
[52] U.S. Cl. .................................. 250/345; 250/343; 250/344
[58] Field of Search ........ 250/343, 344, 345, 252.1 A, 250/341

[56] References Cited

U.S. PATENT DOCUMENTS

| | | |
|---|---|---|
| 3,193,676 | 7/1965 | Smart .................................. 250/345 |
| 3,562,522 | 2/1971 | Cederstrand ..................... 250/252.1 |
| 4,204,768 | 5/1980 | N'Guyen ........................ 250/343 X |
| 5,003,175 | 3/1991 | Fabinski et al. ..................... 250/345 |

FOREIGN PATENT DOCUMENTS 3522949 1/1987 Fed. Rep. of Germany ... 250/252.1

Primary Examiner—Constantine Hannaher
Assistant Examiner—Edward J. Glick
Attorney, Agent, or Firm—R. H. Siegemund

[57] ABSTRACT

Compensation and calibration method for a nondispersive infrared gas analyzer which includes an infrared source of radiation, a measuring path, a reference path, modulation devices, a detector for differential pressure measuring, comprises the following steps: first and prior to measurement, the reference gas having a variable basic concentration in the measuring component is forced through the reference branch and through the measuring branch and the detector is set to a zero position; next a dual calibration chamber is placed into the two reference paths while both of them are still passed through by the reference gas, one of the calibration chambers including a particular concentration in the measuring gas the other one lacking that measuring gas; now the sensitivity and amplification of the detector that obtains as a result of changes in the radiation on account of placing the calibration chamber into the reference and measuring path is adjusted, whereupon the calibration chamber is removed, reference gas still is passed through the reference chamber, while measuring gas now flows through the measuring chamber.

2 Claims, 1 Drawing Sheet

CALIBRATING A NONDISPERSIVE INFRARED GAS ANALYZER

BACKGROUND OF THE INVENTION

The present invention relates to a method for range and offset adjustment and calibration of nondispersive infrared gas analyzer provided for the determination of concentration of a gas component having a basic concentration that is relatively high while the variations in concentration that are of interest cover but a relatively small level and range.

Gas measuring engineering and technology is frequently faced with the task of measuring a gas component and constituent, as well as variations thereof which are basically very small as compared to a "background" of a relatively large basic concentration. This measuring problem at hand is complicated particularly when the basic concentration of the measuring component changes continuously or frequently, thereby obliterating the range and variance of interest. An example is the measurement of assimilation on the basis of the heretofore used optical methods. Here one uses the so called Lambert-Beer law which yields a nonlinear relation between the absorption of light radiation on the one hand, and concentration of a gas in the medium passed through by the light on the other hand. If the sensitivity changes in time depending on the basic concentration, one has to provide a continuous range tracking.

In the example mentioned above the assimilation of interest involves the CO2 content in air. This concentration, considered as a background, may depend on conditions that vary between about 320 ppm and 1000 ppm. Since the assimilation covers only small variations such as 50 ppm in the CO2 value measuring range. background variations can easily obliterate measurement errors up to 50% and more may readily arise.

DESCRIPTION OF THE INVENTION

It is an object of the present invention to provide a new and improved method of operating a nondispersive infrared gas analyzer for measuring the gas concentration over and above or on the basis of and with reference to a basic concentration which is variable, to obtain a variable concentration measurement wherein the measuring sensitivity of the component remains independent from the basic concentration and its variations.

It is therefore a specific object of the present invention to provide a sensitivity adjustment, offset controlling and range setting method for nondispersive infrared gas analyzer, for the determination of the concentration of a gas component by means of a device that includes an infrared radiation source, a sample and reference chamber arrangement which normally provides for measuring gas as well as reference gas, and these two chambers are situated in two separate beam paths originating at the source and are thus traversed by separate rays. The rays are usually continously interrupted for modulation purposes. Furthermore the device used in the method includes a receiving or detection chamber either filled with an absorbing gas that corresponds to the measuring gas or it is itself the measuring gas. The radiation beams will be absorbed by separated chambers in the detection device. A pneumatic pressure sensitive device is connected to the two detection chambers providing an electrical signal that is responsive to the pressure difference in the two detection chambers as an indication of differentiation in the absorption of the radiation that has traversed the reference chamber and measuring gas chamber respectively.

In accordance with the preferred embodiment of the present invention the objects are attained specifically, in that in a first method step, preceding measurement proper, the reference gas with an actual basic "background" concentration flows simultaneously through the measuring chamber and through the reference chamber to obtain and set a zero reference point for gas analysis. In a second and subsequent step also preceding the measurement proper, a calibration chamber is shifted in alignment with the measuring and the reference chambers, which calibration chamber has a portion filled with the measuring component of a very accurately known concentration which corresponds to the desired measurement range; subsequently the sensitivity of the detector generating the electrical signal (i.e. the detector that responds to the pressure difference resulting from this manipulation) will be adjusted so that its sensitivity corresponds to that measuring range. Finally and following the preceding steps the calibration chamber is removed for regular operation wherein the reference chamber receives the same background gas as reference gas as per the first step, but the measuring chamber receives real measuring gas to obtain measurements.

The method that is proposed here precedes measurement proper. The reference gas is for example branched off the measuring gas, i.e. the same gas is used as reference gas, as host gas to which the source of measuring gas is exposed. The problem results from the fact that the reference gas has already, as a background, the same gas that is the measuring gas corresponding to a basic concentration; variations in the background may falsify the measurement. This reference gas which includes interfering measuring gas is used to set the basic response level of the equipment to serve as point of departure for determining the sensitivity of the measurement with reference to the basic concentration of measuring gas as background. This procedure involves these following steps.

First the reference gas with the actual background content of measuring gas is fed to both the measuring chambers and to the reference chambers of the gas analyzer. This step permits a setting of a and set a zero point for that instrument. In the second step a calibration chamber is shifted into the radiation path of both measuring and reference beam paths. One of the calibration chambers is filled with some of the measuring component variety at a predetermined concentration. For example, a measuring range' is thereby defined being about 50 ppm by way of example. The sensitivity of the instrument is now adjusted so that the measuring range covered by the instrument is equal to that particular range, from the previously adjusted zero level to, say 50 ppm, measurement within which the measuring component can vary. Following this the instrument is actually correctly adjusted to the desired measuring range as far as sensitivity is concerned and normal measurement may not proceed.

In case the basic concentration of the host and reference gas will later on change, then these two steps have to be repeated. One can for example provide for an automated basis which repeatedly provides a readjustment and recalibration procedure conceivably any variation in the basic concentration of the measuring gas may be tracked separately to insitute and control the performing of recalibration as desired. This way one obtains a quasicontinuous correction of sensitivity.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Figure 1:
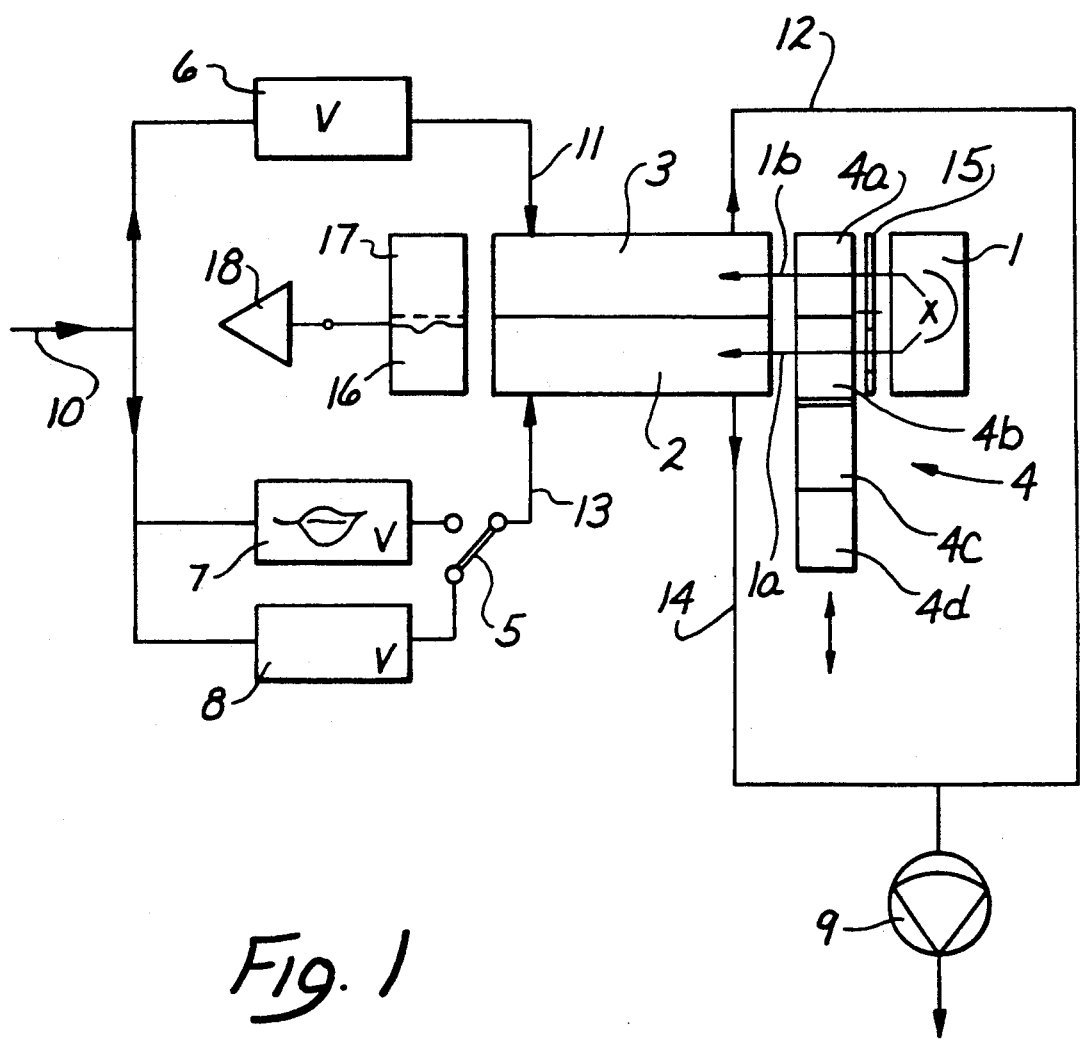
FIG. 1 shows the measuring device for measuring the assimilation of CO2 by a green leaf, under utilization of an IR gas analyzer.

The gas analyzer is basically of known construction; it includes an IR source 1 sending radiation into a measuring branch 1 and 2 and into a reference branch 1-3. In front of the source a modulating diaphragm 15 rotates in a conventional manner changing the two beams to provide for a basic modulation. The reference numeral 2 refers to a measuring chamber that is normally passed through the gas, and parallel thereto is provided a reference chamber 3 that includes or is being passed through by a reference gas. A basic, physical set up of this kind is shown for example in U.S. Pat. Ser. No. 359,510 (filed 06/01/1989, now U.S. Pat. No. 5,003,175). These two chambers are of course physically separated from each other but they are individually traversed by the two beams of radiation 1-2 and 1-3. The radiation in each instance having passed through the chamber 2 or 3, as the case may be, is received in detection chambers 16, 17 respectively. These two chambers pertain to a detector having a pressure sensitive branch by means of which the pressure differential in the two chambers 16, 17 is ascertained on a running basis.

The pressure differential is ascertained by the somewhat schematically indicated detector 18. These aspects are known by and in themselves and do not constitute the part of invention. See also the following U.S. patents as representative examples: U.S. Pat. Nos. 4,682,031; 4,373,137; 4,180,732; 4,156,812.

In the foregoing, the basic set up for infrared nondispersive gas analyzing measurement was described; we now proceed to the description of the inventive calibration procedure. It may now be assumed that the reference gas is air which by means of pump 9 is fed from a conduit 10 through the measuring system. A first branch includes a comparing or reference vessel 6 having a volume V. The gas is passed on through a conduit 11 and into the reference chamber 3. This particular procedure is consistently carried out as a part of the method. The gas, as it is removed from the chamber 3, flows through a branch 12 leading to the pump 9. The pump operates in the suction mode.

A part of the air that is sucked through the conduit 10 will flow into another branch that may include a measuring vessel 7 with the same volume V, and as schematically indicated that measuring chamber 7 may include a leaf as a sink for CO2. Depending upon the position of a valve-switch 5 (alternative) the air that has passed through the chamber 7 will be fed into the conduit 13 and passes into the measuring chamber 2. Conduit 14 refers to the removal path for the measuring gas; everything is pumped out of the system by pump 9.

The switch valve 5 connects the chamber 7 in the normal mode of measurement to the measuring chamber 2. The figure illustrates an alternative connection for the calibration mode. It can be seen that the pump 9 sucks air that enters the system through the conduit 10 into a first branch that includes the vessel 6, conduit 11 reference chamber 3, conduit 12 and out into the pump, while a parallel branch runs from conduit 10 to the measuring vessel 7, the valve 5, the feeder line 13, the measuring chamber 2 and the output branch, conduit 14 thereof, to be united with the air that is arriving through the conduit 12.

If the pump is in continuous operation, of course, no back feeding is expected. The measuring vessel 7 is of course the chamber in which the desired assimilation process obtains. The resulting gases emerging from the leaf mix with the reference air but prior thereto the relative component here is measured by the instrument.

A vessel 8 is connected in parallel to measuring source 7. Vessel 8 has the same volume as the measuring source vessel 7. This vessel 8 has an input duct that is also connected to the conduit 10. In the illustrated position of valve 5, air is in fact sucked through vessel 8 rather than through chamber 7. In this calibration case the measuring chamber 2 receives also reference gas.

As was mentioned earlier the "normal" CO2 content in air may vary from 320 ppm to about 1000 ppm. On the other hand the assimilation of CO varies within a smaller range such as the range from zero to about 50 ppm. it can readily be seen that the background CO2 of the reference/host gas air may vary over a much larger range. That may not happen directly but unforseen changes in CO2 content, even sudden ones, must be expected.

The variation in basic concentration is eliminated by the inventive method in order to obtain a removal of the concomitant error. This procedure is carried out as follows. First, air having whatever basic concentration in CO2 happens to obtain, is also fed into the measuring chamber 2 through the valve 5 having the illustrated position and bypassing leaf chamber 7. In other words chambers 2 and 3 receive the same kind of gas having a basic concentration of CO2 whatever the situation happens to be. As a consequence, specific radiation absorption processes occur in chambers 2 and 3. Aside from certain basic errors, this absorption should result in similar detection processes for both branches. Any inequality reflects instrument inaccuracies which are also eliminated by this procedure. Whatever happens which is to be indicated by 18 under these references and conditions, the output of the detector 18 is now set to zero.

The figure shows also a device 4, which is a calibration. The figure also shows a device 4, which is a calibration U.S. Pat. (Ser. No. 359,510, filed 06/01/1989). Device 4 includes four chambers 4a, 4b, 4c and 4d. During this first step, when chambers 2 and 3 receive reference gas, chambers 4a and 4b are in the illustrative position, just downstream from the chopper wheel and modulator 15. The chambers 4a and 4b are filled with a neutral gas, that is, a gas which has no absorption bands overlapping with absorption bands of the measuring gas (e.g. CO2).

Following the zero setting as described, the calibration chamber 4 is shifted to the alternative position in which chambers 4c and 4d are aligned with chambers 3 and 2. Calibration chamber 4c is again filled with that neutral gas, and so is chamber 4d, but either the latter or the frame is in addition filled with measuring gas, i.e. it is either filled with the measuring component that is CO2 or with a gas having the same kind of IR absorbing properties. The concentration of this gas in chamber 4d (or 4c) is selected to cover a measuring range that is equal to the measuring range of the assimilation process. It may include a 50 ppm concentration in CO2. Please note that this measuring gas may be put into chamber 4c (for placement in the reference path) if the measuring process actually involves absorption (assimilation) of measuring gas. The object in measuring chamber 7 may actually be a sink rather than a source, but owing to the overall symmetry involved it makes no difference whether the measuring gas component is determined on an additive or subtractive basis; one just has to adjust the range accordingly!

The calibration chamber 4 when having chamber 4c and 4d placed into the reference and measuring paths, permits the sensitivity of the detector 18 to be adjusted. In other words what is adjusted is the amplification factor because there should be a particular output that should be equal to (i.e. represent) the concentration of 50 ppm. Following these two calibration processes the calibration chamber, i.e. the two neutral gas containing chambers 4a and 4b, are respectively placed both into the reference and measuring paths. Valve 5 changes position to reconnect measuring chamber 7 to the system. Now normal measurement commences or is resumed.

The gas analyzer is now adjusted correctly to cover the desired measuring range as far as sensitivity is concerned. If for any reason the basic concentration in CO2 varies in the air then the compensation offset and calibration procedure as described has to be repeated. This repetition can well be carried out automatically, it can even be carried out on a temporal basis and/or it may be instigated through separate independently carried out CO2 measurements. In either case a quasicontinuous correction obtains in the sensitivity of the measuring procedure.

The invention is not limited to the embodiments described above but all changes and modifications thereof, not constituting departures from the spirit and scope of the invention, are intended to be included.

We claim:

1. Compensation and calibration method for a nondispersive infrared gas analyzer which includes an infrared source of radiation, a measuring branch, having a measuring path, a reference branch having a measuring path, modulation devices, a detector that includes a detection chamber for the measuring branch and a detection chamber for the reference branch, said detector further including differential pressure measuring structure in order to measure the differences in absorption in the reference branch and measuring branch, comprising the following steps:

as a first step, prior to measurement, passing a reference gas having a variable basic concentration in a measuring component through the reference branch and through the measuring branch and setting the detector to a zero position;

as a second step, placing a dual calibration chamber into the two measuring paths while both branches are still passed through by the reference gas, one of the calibration chambers including a particular concentration in the measuring gas the other one lacking that measuring gas;

adjusting the sensitivity and amplification of the detector that obtains as a result of changes in the radiation on account of placing the calibration chamber into the two measuring paths; and removing the calibration chamber, but continuing to pass reference gas through the reference branch, while passing measuring gas through the measuring branch.

2. Method as in claim 1, as applied for measuring CO2 assimilation, the reference gas being regular air.

* * * * *